United States Patent [19]

Otto, Jr.

[11] 3,967,126

[45] June 29, 1976

[54] X-RAY APPARATUS HAVING TABLE WITH IMPROVED TOP

[75] Inventor: George W. Otto, Jr., Elmhurst, Ill.

[73] Assignee: American Radiologic Systems Inc., Melrose Park, Ill.

[22] Filed: Feb. 20, 1975

[21] Appl. No.: 551,370

[52] U.S. Cl. .............................................. 250/439
[51] Int. Cl.² ......................................... G01N 21/00
[58] Field of Search ........................... 250/439, 452

[56] References Cited
UNITED STATES PATENTS

| | | | |
|---|---|---|---|
| 2,024,351 | 12/1935 | Fischer et al. | 250/439 |
| 2,898,471 | 8/1959 | Kizaur | 250/439 |

*Primary Examiner*—Alfred E. Smith
*Assistant Examiner*—T. N. Grigsby
*Attorney, Agent, or Firm*—Olson, Trexler, Wolters, Bushnell & Fosse, Ltd.

[57] ABSTRACT

X-Ray apparatus comprises a table with an improved top having opposed longitudinal frame members at its sides and a comparatively thin panel extending therebetween. The thin panel is capable of supporting substantial weight due to the panel being maintained in continuous tension. This tension is effected by fasteners which secure end members to the longitudinal frame members and impose forces in opposite directions on the panel transversely thereof. The thin panel permits the patient to be positioned closer to the plane of the X-ray film in the bucky below the table top and also provides a structure which absorbs a relatively small amount of X-ray radiation.

7 Claims, 8 Drawing Figures

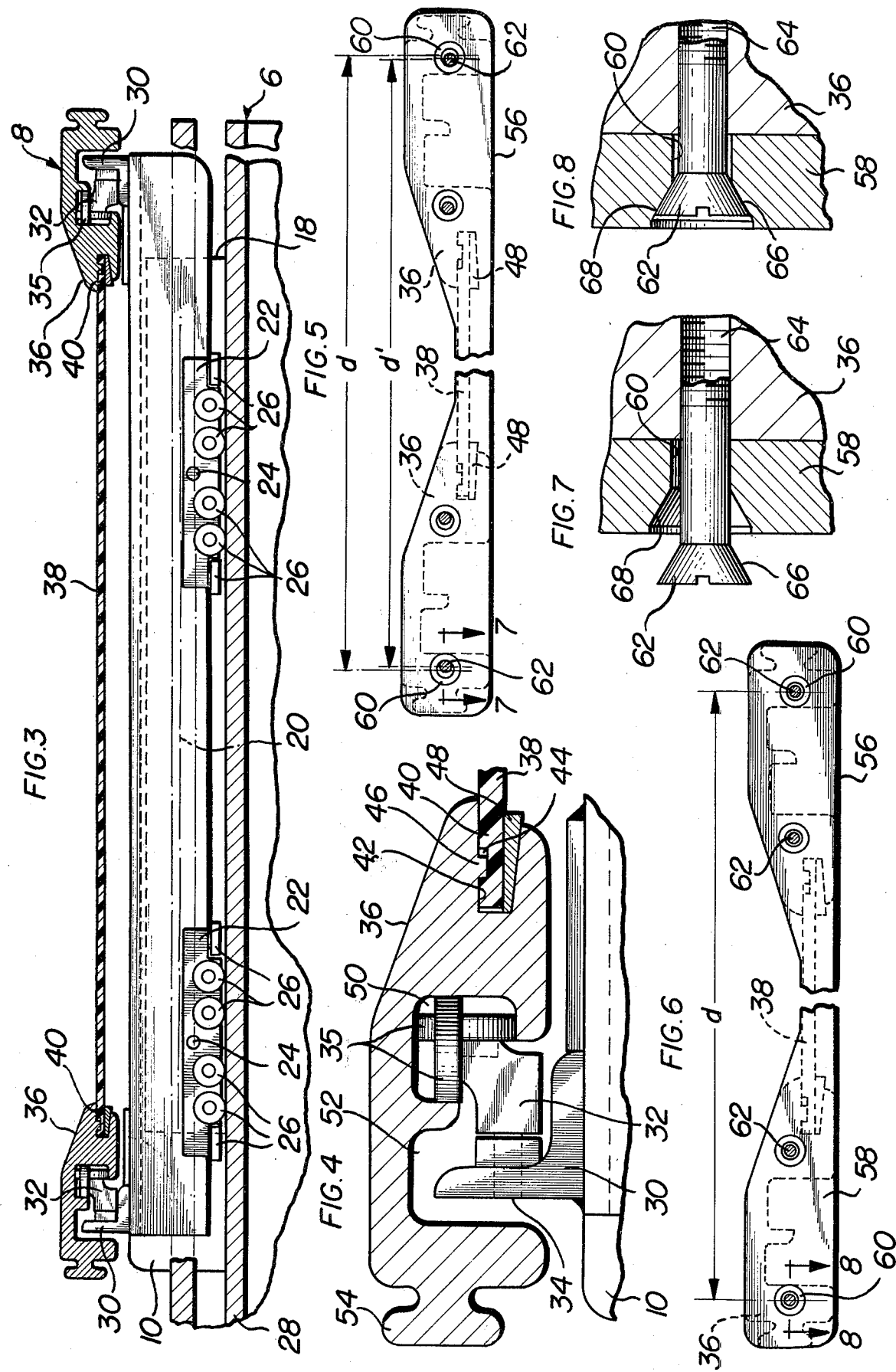

X-RAY APPARATUS HAVING TABLE WITH IMPROVED TOP

BACKGROUND OF THE INVENTION

This invention relates to improvements in X-ray apparatus, and more particularly to diagnostic X-ray apparatus that includes a table with an improved top.

One known type of X-ray apparatus for diagnostic purposes includes an X-ray table having a top upon which the patient is positioned during the procedure. There is generally an X-ray source above the table top and a bucky below the table top, the bucky including an X-ray film casette or carrier that positions the plane of the film substantially parallel to the table top. When a bucky radiograph is taken, it is desirable that the patient be as close as possible to the plane of the X-ray film in order to produce an X-ray exposure with the best possible definition. Furthermore, the table top should not be of the type that absorbs too much radiation as this would require excessive exposure to the patient. Accordingly, from the point of view (1) of reducing the amount of X-ray exposure to the patient and (2) providing an X-ray exposure of good quality, it is desirable that the table top position the patient close to the film plane and also be of a construction that absorbs a minimum of X-rays.

OBJECTS AND SUMMARY OF THE INVENTION

An object of the present invention is to provide an X-ray apparatus having an improved table top which supports the patient relatively close to the plane of the X-ray film, and yet is a top capable of supporting a weight of substantial magnitude, i.e. in the order of four hundred pounds. A table top that supports this amount of weight is considered to be more than adequate for general diagnostic work.

A further object of this invention is to provide an X-ray table with an improved table top that is of relatively inexpensive construction and is light in weight despite its relatively great strength in terms of its ability to support heavy loads. The top is also one that is relatively thin and is of a material that absorbs only a comparatively small amount of X-ray radiation.

The foregoing objects are accomplished, generally speaking, by providing a table top with opposed longitudinal frame members at opposite sides of the top. The frame members may be aluminum extrusions. A panel of relatively thin material extends between the same members. The panel may be a resinous impregnated paper structure, and is secured to the frame members by wedges and/or other securing means. The panel is relatively thin as compared to the thickness of the frame members. An important aspect of the invention lies in the fact that the panel is maintained in continuous transverse tension. This tension is developed as the table top components are being assembled. In the preferred form of the invention, the tension may be developed in the panel as end frame members are secured to the longitudinal frame members with fasteners. These fasteners thread into the longitudinal frame members and cooperate with holes in the end frame members to cam forcefully the longitudinal frame members away from each other and thereby apply tension forces in opposite directions on the panel transversely thereof. Thus, by pretensioning the panel it is capable of supporting substantial weight, and by having the panel thin and of a paper base resinous material, the panel absorbs a relatively small quantity of radiation and may position the patient close to the plane of the film in the casette below the top.

BRIEF DESCRIPTION OF THE FIGURES

FIG. 3 is a fragmentary sectional view taken along line 3—3 of FIG. 1;

FIG. 4 is an enlarged fragmentary sectional view of a portion of FIG. 3;

FIG. 5 is a fragmentary end view of the table top and showing an end frame member in an initial position of attachment of the longitudinal frame members;

FIG. 6 is a view similar to FIG. 5 and showing an end frame member in a final position of attachment to the longitudinal members and placing the table top panel in tension;

FIG. 7 is a fragmentary sectional view of an enlarged scale taken along line 7—7 of FIG. 5; and FIG. 8 is a fragmentary sectional view on an enlarged scale taken along line 8—8 of FIG. 6.

DETAILED DESCRIPTION

Figure 1:
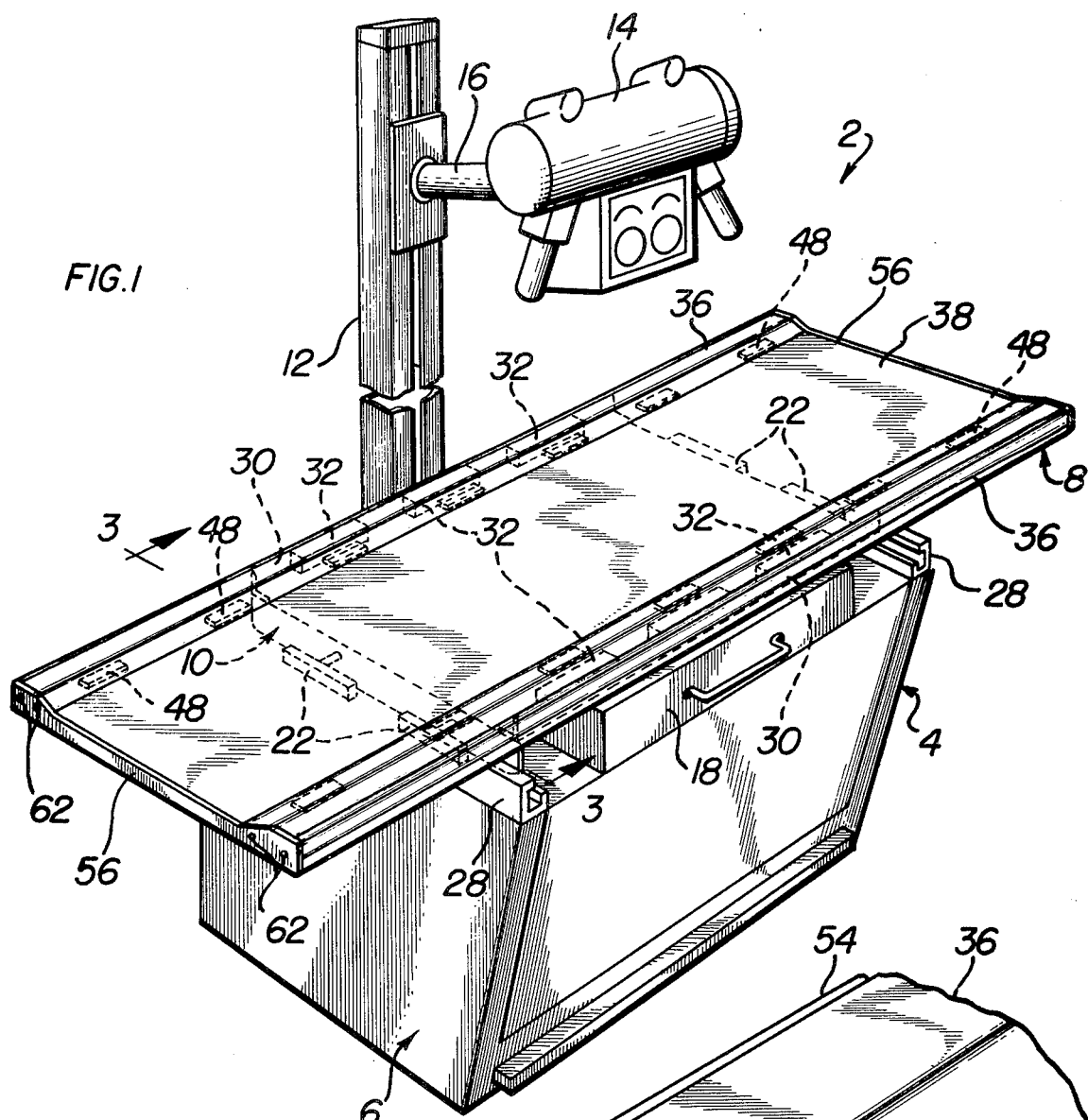
FIG. 1 is a perspective view of X-ray apparatus embodying a table with an improved top constructed in accordance with the present invention.

Referring now in more detail to the drawing there is shown in FIG. 1 an X-ray apparatus 2 that comprises an X-ray table 4 having a base or pedestal 6 and a top 8. The base 6 may be of any suitable configuration as, for example, the generally rectangular configuration shown in FIG. 1. The base 6 may constitute a container or housing for a high voltage X-ray transformer and other control equipment used in the operation of the apparatus 2. The base 6 may also include at its upper end a carriage 10 that directly underlies the table top 8 to support the table top 8 for transverse movement, as will presently be more fully described.

The apparatus also includes a tube stand 12 that includes a tube arm 16. The tube arm 16 is a cantilever that supports a housing 14 containing an X-ray tube that is normally positioned above the table top 8.

Below the table top 8 is a bucky 18 that includes an X-ray film carrier or cassette, a bucky grid, and related mechanism for operation the same. The details of these are known and need not be described in detail herein. FIG. 3 shows a broken line 20 that represents the film plane which is about one inch below the top of the bucky housing.

As best seen in FIGS. 1 and 3, the carriage 10 is suitably provided with rollers for supporting the carriage 10 on the base 6 so that the carriage 10 and the top 8 can jointly move laterally, namely toward and away from the tube stand 12. More particularly, carriage 10 has four roller supports 22, two at each end of the carriage. Each support 22 is rockably secured by a pin 24 to a side portion of the carriage 10. The roller supports 22 each carry a series of rollers 26 which roll in opposed, transverse tracks 28,28 that are rigidly attached to and form part of the base 6. It will be noted from FIG. 1 that the cross section of each track 28 is a modified C-shape such as to support rollably both horizontal and vertical rollers 26, as shown in FIG. 3. This arrangement enhances the stability of the movement of the carriage 10 over the tracks 28,28.

The carriage 10 also has at its opposite sides respective longitudinal angle members 30,30 that are rigidly attached to the carriage to form parts thereof. Mounted on the vertical flange portions of these angle members 30,30 are roller supports 32 which are similar to the roller supports 22 and which carry both vertical and horizontal rollers 35. There are six roller supports 32, three on each side as seen in FIG. 1, and each roller support 32 is rockably secured to its associated angle member 30 by a pin 34 (FIG. 4).

Turning now to the table top 8 it will be seen that the same includes at its sides opposed longitudinal frame members 36,36 which are preferably in the form of aluminum extrusions. Extending between the frame members 36,36 is a panel 38 of a non-metallic material, such as a resinous impregnated structure, for instance a paper base material impregnated with a phenolic resin. The panel 38 may be of the order three-sixteenths of an inch thick. The longitudinal frame members 36,36 are much thicker as compared to the thickness of the panel although they taper inwardly toward the panel. The opposed longitudinal margins 40,40 of the panel 38 are secured to the frame members 36,36 in any suitable manner. In the form of the invention herein shown each frame member 36 has an inwardly presented longitudinal groove 42 that receives an adjacent longitudinal margin 40 of the panel 38. Each margin 40 has a longitudinal notch 44 that receives a longitudinal tongue 46 on a frame member in the groove 42 thereof. A series of wedges 48 are pressed or otherwise forced in the grooves 42 to clinch the margin 40 firmly to the associated longitudinal frame member 36. Accordingly, the panel 38, upon which the patient will be supported during radiography, runs generally parallel to the film plane 20 and is kept fairly close thereto, preferably of the order of about two inches therefrom.

It will be apparent that the top 8 is supported for longitudinal movement relative to the carriage 10 by the horizontal and vertical rollers 35 which engage the surfaces of the frame member within a first cavity 50 (FIG. 4). The frame member 36 also has a second cavity 52 that is laterally outwardly of the first-mentioned cavity 50 to provide clearance for the vertical flange of the angle member 30. Outwardly of the cavity 52 the frame member 36 has an accessory rail 54 for a foot or shoulder rest, compression board, or the like.

From the foregoing it will be seen that the rollers 26,35 and their associated roller supports 22,32 movably support the table top 8 for longitudinal and transverse movement within the limits of movement permitted by the design of the table structure. Normally the relatively thin panel 38 would not be capable of adequately supporting a weight of several hundred pounds, especially if it were made out of the materials heretofore described and were of a width suitable for that of an X-ray table, for instance about 23 inches. However, the present invention provides a way of utilizing the thin panel, and this is done by introducing tension in the panel 38 transversely thereof to increase its effective strength, and as will now be presently described.

Figure 2:
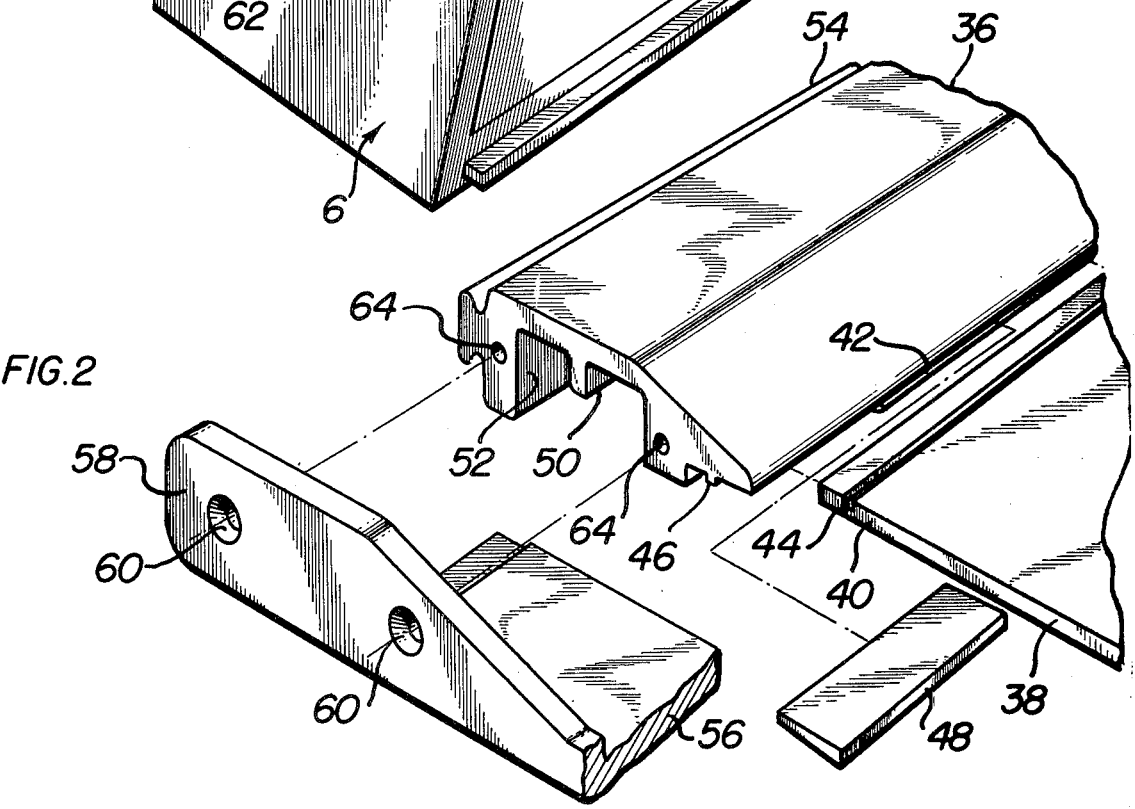
FIG. 2 is an enlarged exploded fragmentary perspective view of a corner of the table top of FIG. 1.

The table top 8 includes end frame members 56,56 one at each end of the top 8. Each frame member 56 may also be of aluminum and may have a generally angle or L shaped cross section when viewed transversely, as best seen in FIG. 2. Each end frame includes a vertical flange 58 portion which is shaped with an outline somewhat companion to the maximum dimensions of the longitudinal member 36 for appearance purposes. The horizontal flange portion of the member 56 underlies the adjacent transverse margin of the panel 38 and the adjacent transverse margins of the members 36,36. The flange 58 of each end frame member 56 includes spaced holes 60,60 for receiving screw-threaded fasteners 62 which thread into threaded holes 64,64 in the adjacent transverse end faces of the longitudinal frame members 36,36. As best seen in FIGS. 7 and 8, each fastener 62 has a head with a conical surface 66 that engages the conical surface 68 of the countersunk portion of the hole 60 whereby the conical surfaces 66 provide cam surfaces that engage the follower surfaces 68 in the end frame members 36. As seen in FIGS. 7 and 8, the diameter of the holes 60 is oversized as compared to the diameter of the shank of the fastener 62 therein so that there is substantial radial clearance therebetween. This permits movement of the fastener 62 in the hole 60 laterally outwardly, namely toward the adjacent accessory rail 54.

It will be noted from FIG. 5 that when the fastener 62 is initially inserted into the hole 60 and threaded into the hole 64 the center of the hole 60 will be eccentric to the center of the hole 64. Thus, the distance between the centers of the two outermost holes 60,60 will be $d$ as shown in FIG. 5. The distance between the center line of the two outermost holes 64 (which is the same as the center-to-center distance between the two outermost associated fasteners 62 of FIG. 5) will be a distance $d'$. Upon tightening of the fastener 62, the distance $d'$ will increase and approach the distance $d$ so that they are the same or nearly the same. This occurs because for each fastener 62 the surface 66 engages the surface 68 in a manner tending to center the fastener in its hole 60, thereby increasing $d'$. When all screws 62 are tightened, such action imposes forces on the frame members 36,36 which in turn impose forces on panel 38 in opposite directions transversely thereof to place the panel in tension. The tightening of all light screws 62 (four at each end of the top 8) thus applies forces in opposite directions on the panel 38 at the transverse margins (i.e. opposite ends) of the panel wherein the end frame members 56,56 are mounted. This tension is maintained as long as the screws 62 are tight, which they can be presumed to be at all times after assembly of the top 8. The tension in the panel 38 remains notwithstanding the longitudinal transverse movement of the table top 8 with a patient thereon. The tension serves to rigidify and inhibit sagging of the relatively thin panel. Furthermore the tension extends throughout the full length of the panel 38.

The engagement of the tongues 46 with the grooves 44 facilitates tensioning the panel 38 upon spreading apart of the frame members 36 during tightening down of the screws 62 due to the pulling forces being transmitted by the tongue 46. Thus, the grip between the frame member 36 and the panel margin 40 does not depend exclusively on the wedges 48, although the wedges 48 allow for a pre-assembly of the members 36 and panel 38.

I claim:

1. In an X-ray apparatus comprising a table having a base, a top, and a bucky below the table top; said top having opposed longitudinal frame members at opposed sides of said top and with a panel extending transversely between said frame members. the panel having opposed longitudinal margins joined to said frame members, the frame members being thick as compared to the thickness of the panel, roller means for movably supporting said top in various positions on said base, and means cooperating with said longitudinal members and forming part of said top for imposing continuous transverse tension in said panel whereby said tension remains in said panel when the panel is in said various positions on said base.

2. In an X-ray apparatus according to claim 1, said last-named means comprising end frame members extending transversely of said panel at opposed transverse margins of said panel, and fastener means securing said end frame members to said longitudinal frame members.

3. In an X-ray apparatus according to claim 2, said fastener means engaging said longitudinal frame members and imposing forces in opposite directions transversely of said panel.

4. In an X-ray apparatus according to claim 3, said fastener means having cam-forming surfaces that engage openings in said end frame members.

5. In an X-ray apparatus having table with a table top and wherein there is an X-ray film carrier below the table top and an X-ray source above the table top, an improvement in the table top comprising an elongated panel parallel to the film plane of the film carrier and having transverse margins, and means imposing continuous transverse tension on said panel, said means comprising end frame structure at said transverse margins that apply forces in opposite directions on said panel transversely thereof.

6. In an X-ray apparatus having table with a table top and wherein there is an X-ray film carrier below the table top and an X-ray source above the table top, an improvement in the table top comprising an elongated panel parallel to the film plane of the film carrier, and means imposing continuous transverse tension on said panel, said means comprising structure at said transverse margins that apply forces in opposite directions on said panel transversely thereof, said top including frame members at opposed longitudinal margins, said frame members having grooves for receiving said longitudinal margins, and means cooperating with said frame members and panel for maintaining said longitudinal margins in said grooves.

7. In an X-ray apparatus according to claim 6, said frame members being metallic and said panel is a resinous impregnated non-metallic structure.

* * * * *